United States Patent [19]

Gu et al.

[11] Patent Number: 5,018,524

[45] Date of Patent: May 28, 1991

[54] APPARATUS AND METHOD FOR GENERATING VITAL INFORMATION SIGNALS

[76] Inventors: Hansen Gu; Dumin Wu, both of Bldg. 18, Hongxu Rd. 100, Shanghai, China

[21] Appl. No.: 232,536

[22] Filed: Aug. 15, 1988

Related U.S. Application Data

[63] Continuation of Ser. No. 863,201, May 14, 1986, abandoned.

[30] Foreign Application Priority Data

| May 15, 1985 | [CN] | China | 85103600 |
| Aug. 3, 1985 | [CN] | China | 85106040 |
| Apr. 24, 1986 | [CN] | China | 86102850 |

[51] Int. Cl.$^5$ ............................................. A61N 1/32
[52] U.S. Cl. .................................... 128/421; 128/422
[58] Field of Search ............... 128/420 A, 419 R, 421, 128/422, 804, 711, 732, 783, 905, 907

[56] References Cited

U.S. PATENT DOCUMENTS

| 3,181,535 | 5/1965 | Milinowski | 128/422 |
| 3,329,148 | 7/1967 | Kendall | 128/804 |
| 3,650,276 | 3/1972 | Burghele et al. | |
| 3,880,170 | 4/1975 | Popov | 128/421 |
| 3,902,502 | 9/1975 | Liss et al. | 128/422 |
| 3,913,567 | 10/1975 | Streckmann | 128/711 |
| 3,934,267 | 1/1976 | Kosaka et al. | 128/711 |
| 4,016,886 | 4/1977 | Doss et al. | |
| 4,055,190 | 10/1977 | Tany | |
| 4,148,321 | 4/1979 | Wyss et al. | |
| 4,424,812 | 1/1984 | Lesnick | |
| 4,535,777 | 8/1985 | Castel | 128/421 |
| 4,586,509 | 5/1986 | Liss et al. | 128/422 |
| 4,642,769 | 2/1987 | Petrofsky | 128/419 R |
| 4,832,033 | 5/1989 | Maher et al. | 128/421 |

FOREIGN PATENT DOCUMENTS

| 2745349 | 4/1978 | Fed. Rep. of Germany | 128/420 A |
| 2712101 | 10/1978 | Fed. Rep. of Germany | 128/419 R |
| 3335849 | 4/1985 | Fed. Rep. of Germany | 128/420 A |

*Primary Examiner*—Ruth S. Smith

[57] ABSTRACT

The present invention provides an apparatus and a method for generating vital information signals which are formed by a pulse train made up of bursts of the same width and distance, wherein each burst is made up of a given number of pulses of a specific frequency. The apparatus according to the present invention comprises a pulse signal generating means and a signal output circuit for generating pulse signals and shaping their waveforms and structures to meet specific requirements. The method of the present invention generates the above-mentioned signals by means of information recording medium and signal reproducing apparatus, and provides the same for medical or health care uses.

2 Claims, 14 Drawing Sheets

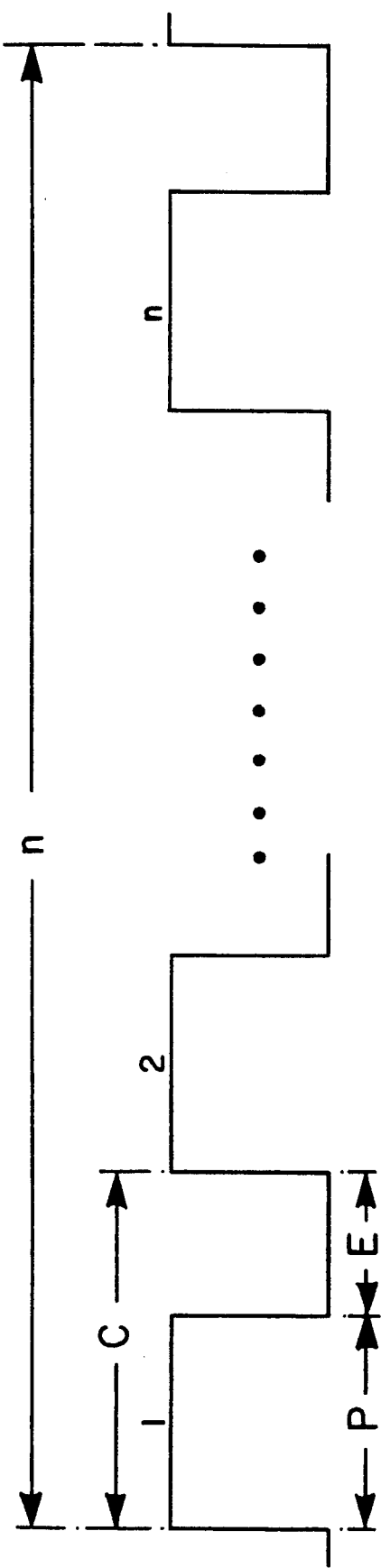
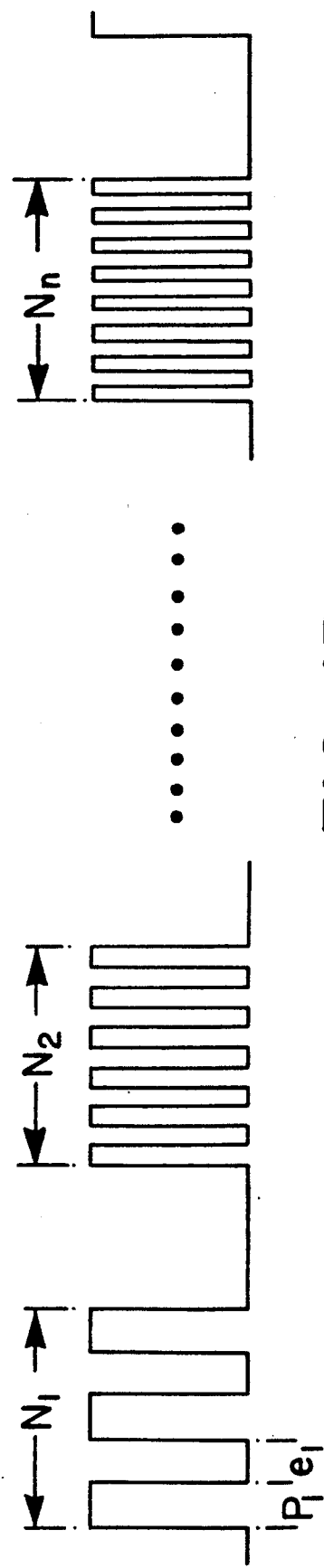
FIG. IA
FIG. IB

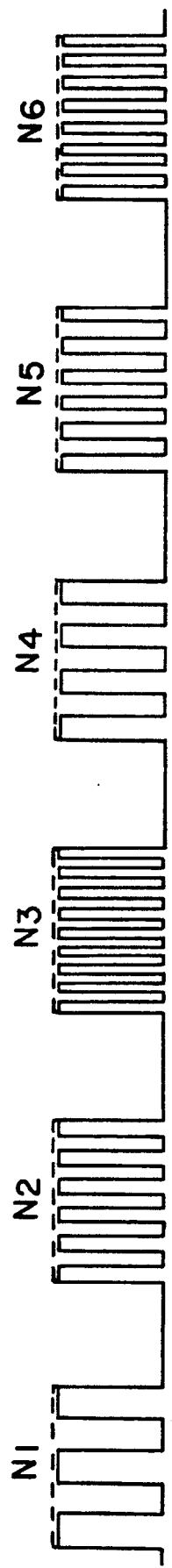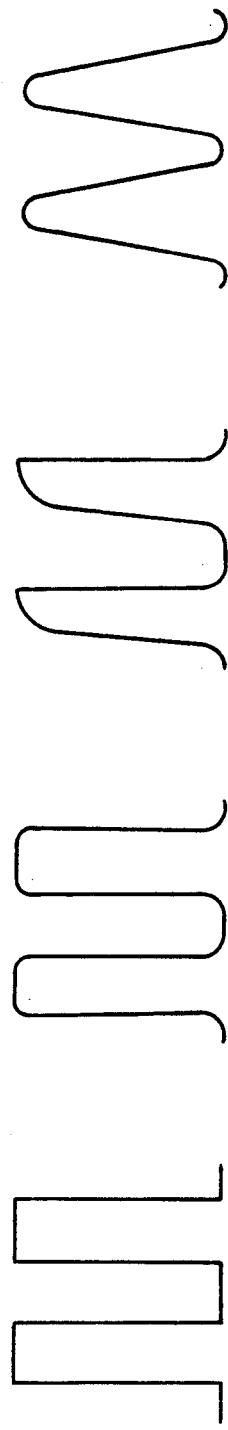

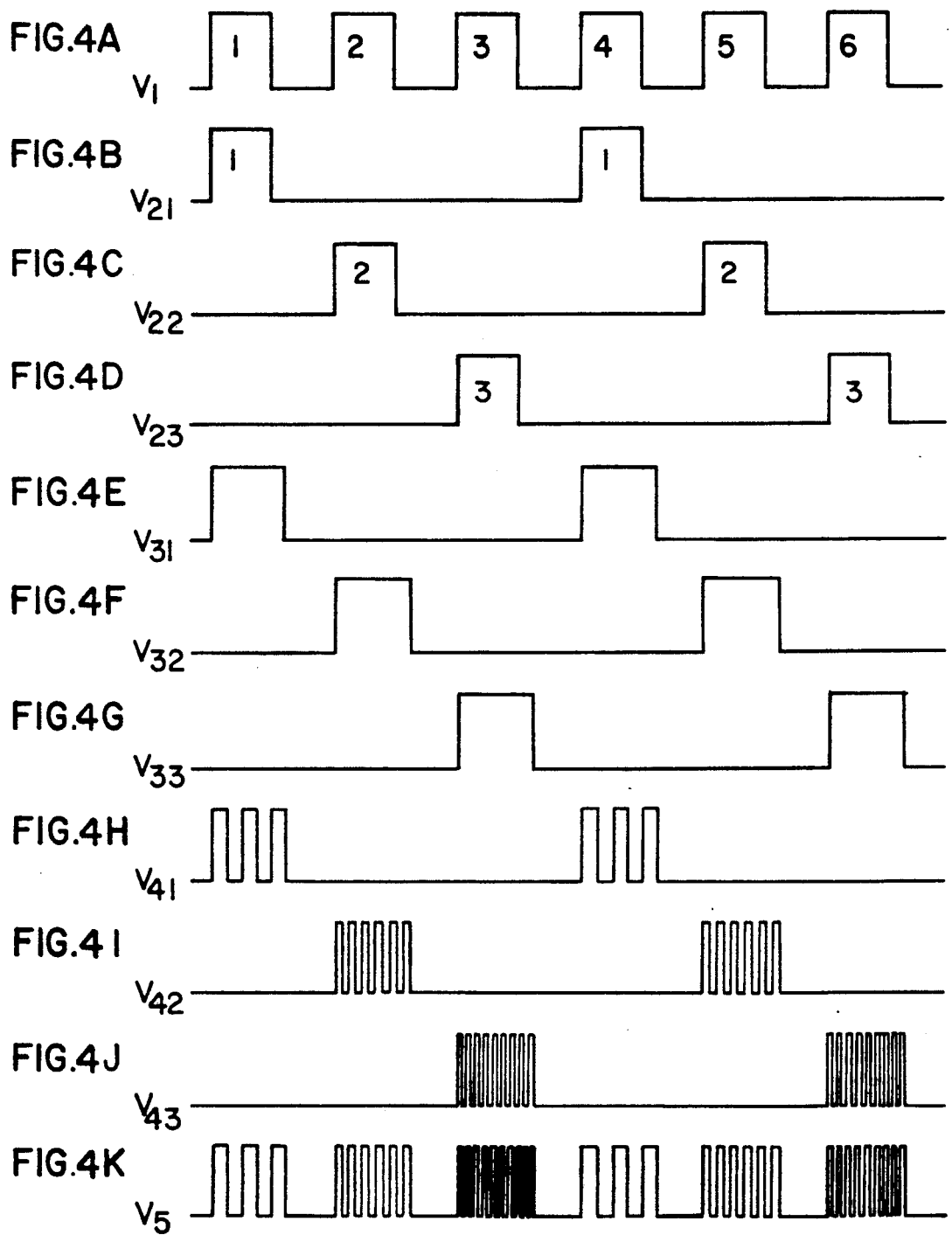

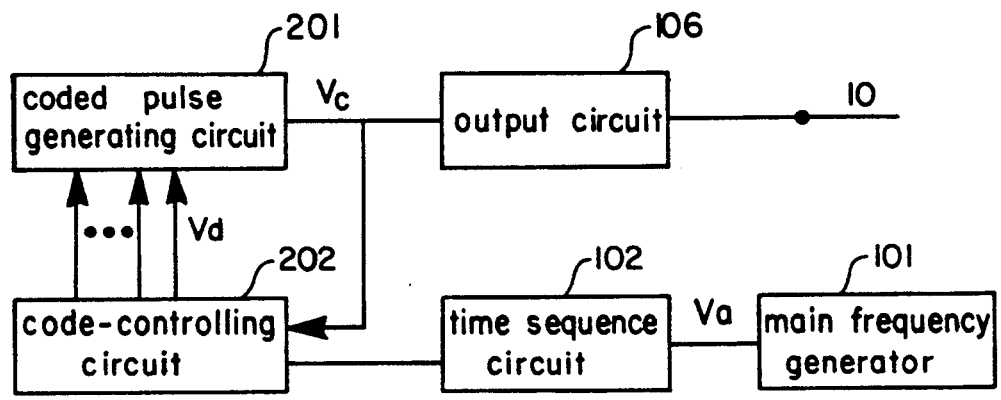
FIG. 5A
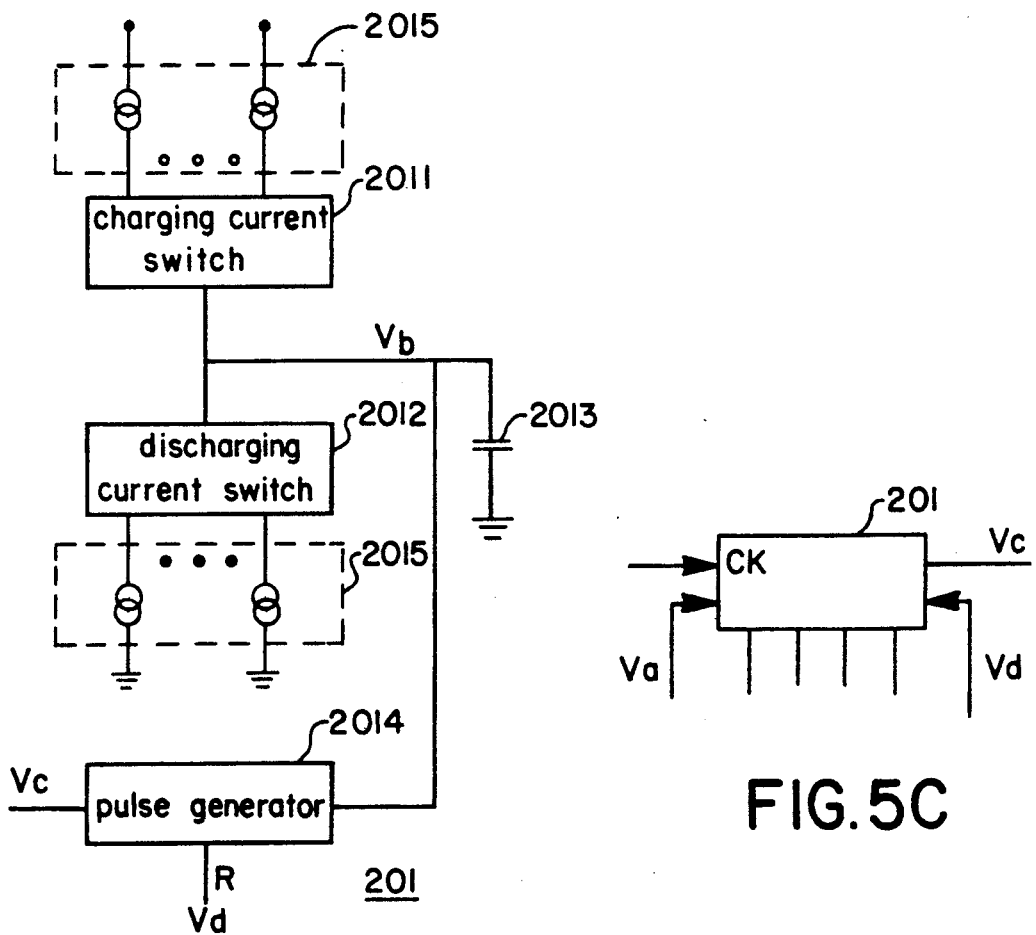
FIG. 5C
FIG. 5B

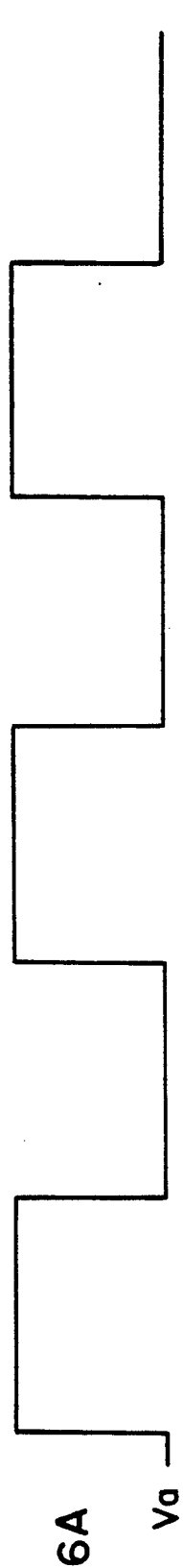
FIG. 6A  Va
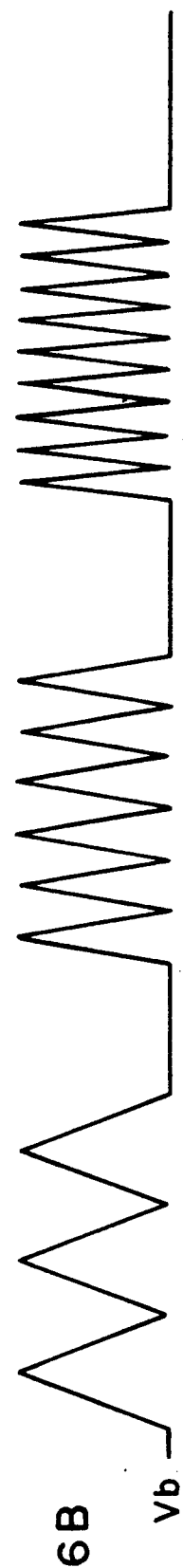
FIG. 6B  Vb
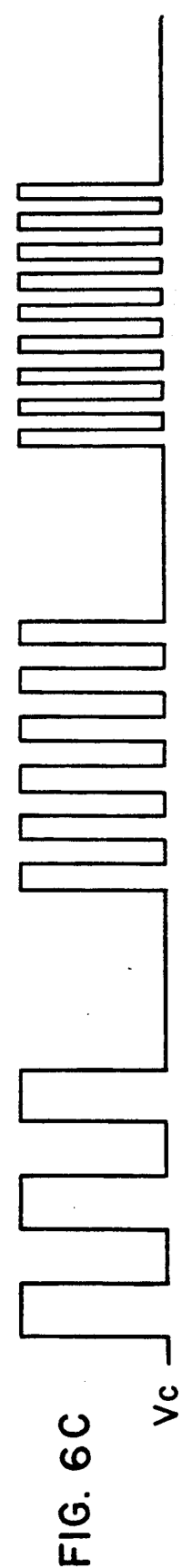
FIG. 6C  Vc
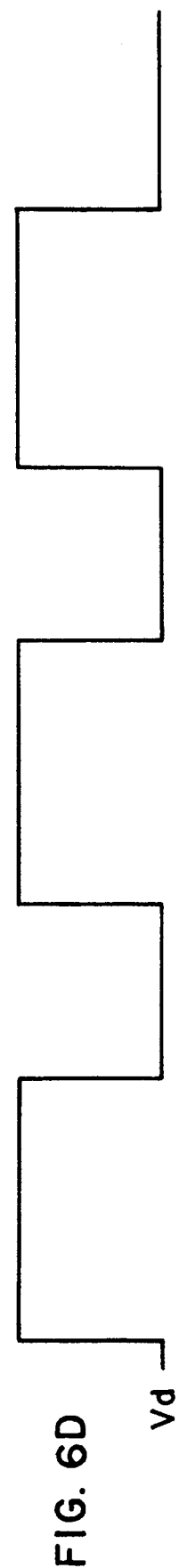
FIG. 6D  Vd

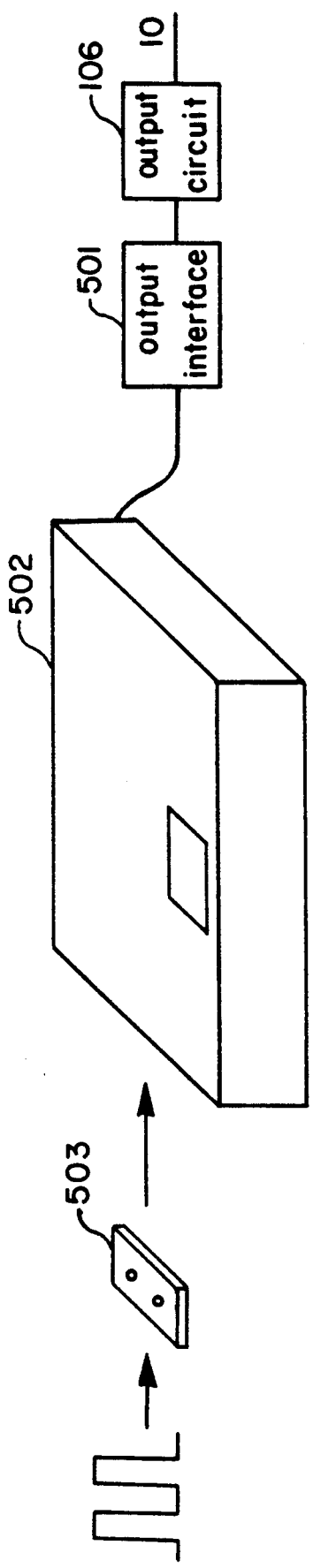
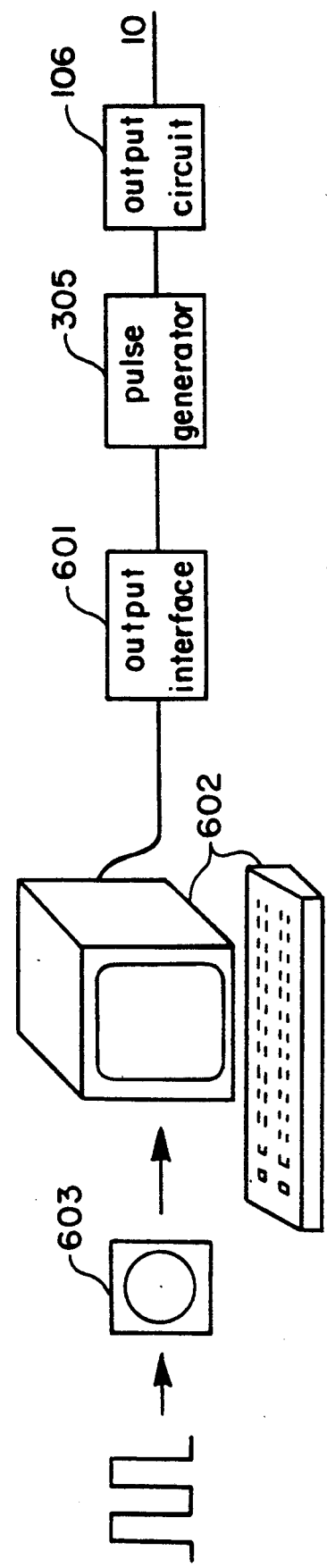
FIG. 10
FIG. 11

APPARATUS AND METHOD FOR GENERATING VITAL INFORMATION SIGNALS

This is a continuation of application Ser. No. 863,201, filed May 14, 1986, now abandoned.

FIELD OF THE INVENTION

The present invention relates to an apparatus and a method for generating vital information signals, particularly, to an apparatus and a method which can generate electric pulses that have specific digital coded sequence at low power levels. Such signals can be used to adjust physiological functions of a living body so as to fulfill, medical and health care purposes.

BACKGROUND OF THE INVENTION

In recent years, basing on the field theory, the information techniques and the theory of the traditional Chinese medicine, Chinese researchers have made extensive researches and a great deal of experiments on the vital information, one of the most important vital characteristics of a living body. Particularly, by means of modern detecting equipments, measuring tests were made on "Fa Gong", an energy emitting phenomena of a "Qi Gong" expert, a deep breathing exercises expert, resulting in remarkable achievements. These research results were reported on "NATURE JOURNAL", Vol 3, No. 8, August, 1980, PP 563–566, published by Shanghai Science and Technology Publishing House, and "SCIENCE YEARBOOK", 1981, PP 1.34–1.41, published by Shanghai Science and Technology Publishing House. The contents of these articles are incorporated herein by reference.

According to the theory of physics, the physical world manifests itself in two kinds of matter, one with static mass, the other without static mass but with energy (different kinds of field). These two kinds of matter are highly correlated and any body with static mass possesses its own natural resonance frequency. A living body can also be treated as a morphology system made up of cells, tissues and organs, as well as an information system made up of different kinds of field matter, such as cell's potential, electrocardiogram, electroencephalogram and different kinds of radiation. The two systems interact on each other and coexist within the same living body.

On the basis of the field theory and the information techniques, the present inventors made researches on the relations between the morphology system and the information system of a living body, and information exchange between the information system and the environment of the living body, so as to utilize the information of field matter to diagnose diseases and, by means of specific signals, to adjust the conditions of the information system of a living body, thus improving the conditions of the morphology system for medical and health care purposes.

In vital information science, researches have been made on the information exchange between a living body and its environment, particularly on the information exchange windows, which include:

information windows through which a living body can selectively receive and emit information signals, and which is represented by specific physical properties, frequency, waveform and strength of the information signals; and address windows which is the capability of different positions on a living body for selectively receiving and emitting information signals, such as acupoints, blood vessels, lymphatic vessels and so on.

Since the vital information is related to the delicate structure of a living body, the vital information signals, different from those of the conventional physiotherapy, have complicated waveform containing a large quantity of information therein. If the right windows on a living body are chosen, great biological activity will be produced by the vital information signals of low power levels and good curative effects to many diseases can be achieved.

In prior art, there are some kinds of apparatus which can generate electric signals with certain waveform for medical or health care use, such as electric acupuncture apparatus, and cardiac pace-maker, etc. However, the quantity of the information contained in the signals generated by these kinds of apparatus is small since they work mainly by their direct physical effects. Yet, the signals of the present invention contain a large quantity of information at low power level, so that they have great biological activity and work through the information contained therein, thus making the present invention essentially different from the prior art.

SUMMARY OF THE INVENTION

By means of modern electronic techniques, the present invention has provided an apparatus and a method for generating vital information signals, whereby to generate a train of bursts which has an envelope in the form of pulse signals with specific frequency and duty cycle. Each burst further contains digital codes that are specially numbered and highly sequenced. Such vital information signals with special waveform at low power levels can be inputted through specific address windows into a living body to fulfill medical and health care purposes.

The apparatus and method provided by the present invention can generate vital information signals of different waveforms, the structure of which waveforms has the following features:

1. highly sequenced digital coded pulse train;
2. the pulse train of the bursts repeat periodically;
3. the specific structure of the waveform is highly correlated with certain physiological functions of a human or an animal body, thus can be used for specific medical or health care purposes; and
4. each of the quantitative parameters of the pulse train (including coding structure, frequency, duty cycle, direct or alternating current components, etc.) should be selected from a strictly limited range, and beyond the allowable range, the signals will lose their original effects and sometimes can even be harmful.

The first embodiment of the apparatus according to the present invention, comprises a main code generating circuit, a sub-code generating circuit, an output circuit and at least one pair of output electrodes.

The second embodiment of the apparatus according to the present invention, comprises a coded pulse generating circuit, a code-controlling circuit, an output circuit and its output electrodes.

The third embodiment of the apparatus according to the present invention, comprises a central processing unit (CPU), a clock circuit, a memory or an input interface, a pulse generator, an output circuit and its output electrodes.

The fourth embodiment of the apparatus according the present invention, comprises a light source, a light-modulating device, a photosensitive device, a device for driving the light-modulating device, an output circuit and its output electrodes.

The present invention also provides a signal attenuating device to be used in the output circuit to attenuate the signals in a relatively wide range of frequency spectrum and to improve the waveform of the output signals so as to achieve a preferred output waveform.

The present invention also provides a method for generating the above-mentioned coded pulse train.

According to a first embodiment of the method of the present invention it comprises the following steps:

recording by, a video signal recording apparatus, the signals generated by the above-mentioned signal generating apparatus of the present invention on a signal recording medium;

reproducing by, a video signal reproducing apparatus, the signal recorded on the recording medium;

shaping and attenuating the above reproduced signals by the output circuit of the present invention; and providing the signals by the electrodes for medical and health care uses.

In the present embodiment of the method, the apparatus for recording and reproducing the video signals can be a conventional tape recorder, and a video disc player, etc.

According to a second embodiment of the method of the present invention, the method comprises the following steps:

programming the above-mentioned pulse train into a computer routine;

inputting the routine into a memory of a computer;

generating and sending out corresponding control signals by a central processing unit according to the routine;

inputting the control signals into a pulse generating circuit to generate the above-mentioned coded pulse train;

shaping and attenuating the pulse train by the output circuit of the present invention; and providing the pulse train by the electrodes for medical and health care uses.

One object of the present invention is to provide a coded pulse train made up of a plurality of strictly sequenced and periodically repeated bursts. The specific waveform structure of the pulse train correlates with certain functions of the vital information system of a human or an animal body; therefore, it can be used to adjust the vital information system, thus fulfilling specific medical or health care purposes.

Another object of the present invention is to provide an apparatus which can generate the electric pulse train with the above-mentioned waveform structure and input said pulse train into specific positions on a human or an animal body for specific medical or health care purposes.

A further object of the present invention is to provide a method for generation of an electric pulse train with the above-mentioned waveform structure and input said pulse train into specific positions on a human or an animal body for specific medical or health care purposes.

A still further object of the present invention is to provide a signal attenuating device which can shape and attenuate the electric pulse train into a preferred waveform.

BRIEF DESCRIPTION OF THE DRAWINGS

The above-mentioned features and objects of the present invention and other advantages and objects thereof will become more apparent in the following detailed description of the present invention in combination with the accompanying drawings, in which:

FIGS. 1A-1E are illustrative diagrams showing the waveform analysis of the vital information signals according to the present invention;

FIGS. 4A-4K is a diagram showing the signal waveform on the corresponding nodes of the circuit shown in FIG. 3;

FIG. 5A-5C are block diagrams showing the second embodiment of the apparatus according to the present invention;

FIG. 6A-6D is a diagram showing the signal waveform on the corresponding nodes shown in the block diagrams of FIGS. 5A and 5B;

FIG. 10 is an illustrative diagram showing the first embodiment of the method according to the present invention;

FIG. 11 is an illustrative diagram showing the second embodiment of the method according to the present invention.

DETAILED DESCRIPTION OF THE INVENTION

Figure 1E:
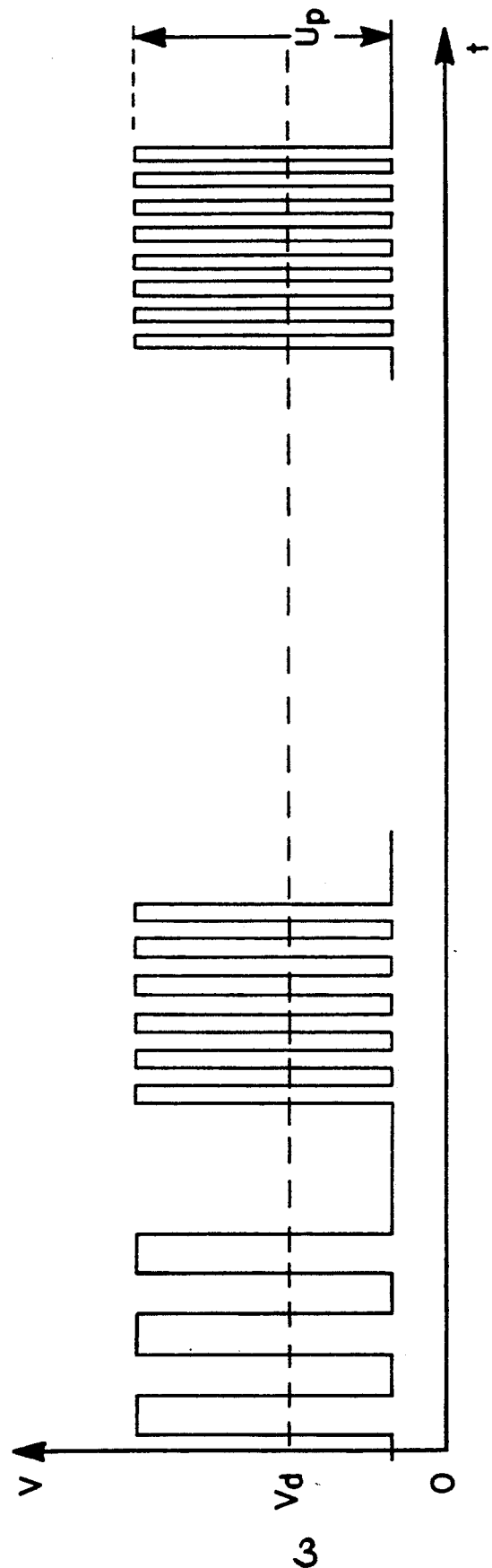

FIGS. 1A-1E are diagrams showing waveform analysis of the vital information signals of the present invention. For the convenience of analysing and understanding, the waveform characteristics of the signals are divided into the envelope characteristics and the characteristics of the bursts enclosed inside the envelope. Both of them are in the form of digital pulses. Thus the analysis can be done in a conventional approach for digital pulses. In the description hereinafter, the envelope is referred to as the main code of the vital information signals while the bursts enclosed therein are referred to as the sub-code of the vital information signals.

In FIG. 1A, the reference character n indicates the time sequence number of the vital information signals according to the presett invention. In different vital information signals, different positive integer n can be selected as the time sequence number, i.e., one cycle of the signals is made up of n main code pulses. The, practical values of n will be explained hereinbelow. The reference character C indicates the time duration of one pulse period of the main code; F indicates the frequency of the main code, $F=1/C$; P indicates the pulse width of the main code; E indicates the distance between two main code pulses; and D indicates the duty cycle of the main code pulses, wherein $D=P/E$. In a group of waveforms of the vital information signals according to the present invention, the main code frequency F and the duty cycle D are constant with F ranging from 230 to 280 KHz and 250 KHz being preferable, and with D ranging from 0.33 to 5.0 and 1.67 being preferable.

FIG. 1B shows the sub-code structure with the main code wavefrom shown in FIG. 1A as the envelope. It can be seen in FIG. 1B that the sub-code pulses are kept within the width of the main code pulses, and within each main code pulse the leading edge of the first sub-code pulse coincides substantially with the leading edge of the main code pulse while the trailing edge of the last subcode code pulse substantially coincides with the trailing edge of the main code pulse. Reference characters $N_1$-$N_n$ indicate respectively the number of sub-code pulses enclosed in each of the main code pulse. It is shown in FIG. 1B that $N_1=3$, $N_2=6$ $N_n=8$. Within the same main code pulse, the pulse width p of each sub-code pulse, the distance e and the duty cycle d, wherein $d=p/e$, are all kept substantially constant. The duty cycle d can be selected from the range of 0.8-1.2 with 1.0 being preferable.

FIG. 1C shows an example of the vital information signals according to the present invention, in which $n=6$. The dash line shown therein represents the waveform of the main code which is not the actual output waveform but the envelope of the signals. The sub-code structures shown in FIG. 1C are $N_1=3$, $N_2=6$, $N_3=9$, $N_4=4$, $N_5=6$, $N_6=8$, F=250KHz, D=1.5 and d=1.0. The waveform is repeated periodically in practical use.

Four kinds of waveform acceptable by the sub-code pulses are shown in FIG. 1D, in which (1) is the square wave, (2) is the square wave with rounded corners, (3) is the integrated wave and (4) is the sine wave. In practical use, the square wave with rounded corners (2) is preferable.

FIG. 1E shows the relation between the magnitude of the vital information signals and time, in which Vd indicates the direct current component of the vital information signals and Up indicates the peak-to-peak voltage of the sub-code pulses; both of them can be respectively selected from the ranges of $O<Vd<1.0$ V and $O<UP<1.5$ V. The sub-code pulses shown in FIGS. 1B-1E are all positive pulses. If negative pulses are used instead, similar effects can also be achieved.

Several examples of the waveform of the vital information signals are shown in Tables 1-4 hereinbelow and their medical effects are explained.

TABLE 1

| n = 6, F: 230–280 KHz, D: 0.33–5.0, d: 0.8–1.2 | | | | | |
|---|---|---|---|---|---|
| $N_1$ | $N_2$ | $N_3$ | $N_4$ | $N_5$ | $N_6$ |
| 3 | 6 | 9 | 4 | 6 | 8 |
| 4 | 6 | 9 | 3 | 6 | 8 |
| 3 | 4 | 6 | 6 | 8 | 9 |
| 3 | 8 | 9 | 4 | 6 | 6 |
| 4 | 8 | 9 | 3 | 6 | 6 |
| 3 | 4 | 9 | 6 | 6 | 8 |
| 3 | 4 | 8 | 6 | 6 | 9 |

Each pulse train indicated in Table 1 can be used to improve the circulatory functions of a human or an animal body and to increase metabolism of the living tissue.

TABLE 2

| n = 4, F: 230–280 KH$_z$, D: 0.33–5.0, d: 0.8–1.2 | | | |
|---|---|---|---|
| $N_1$ | $N_2$ | $N_3$ | $N_4$ |
| 1 | 8 | 2 | 8 |

The pulse train indicated in Table 2 can be used for vision correction with quick effects.

TABLE 3

| n = 2, F: 230–280 KHz, D: 0.33–5.0, d: 0.8–1.2 | |
|---|---|
| $N_1$ | $N_2$ |
| 2 | 8 |

The pulse train indicated in Table 3 can also be used for vision correction with long time effects.

TABLE 4

| n = 2, F: 230–280 KHz, D: 0.33–5.0, d: 0.8–1.2 | |
|---|---|
| $N_1$ | $N_2$ |
| 8 | 9 |

The pulse train indicated in Table 4 can be used to adjust intestinal functions. It can be used to cure both constipation and diarrhoea.

Figure 2:
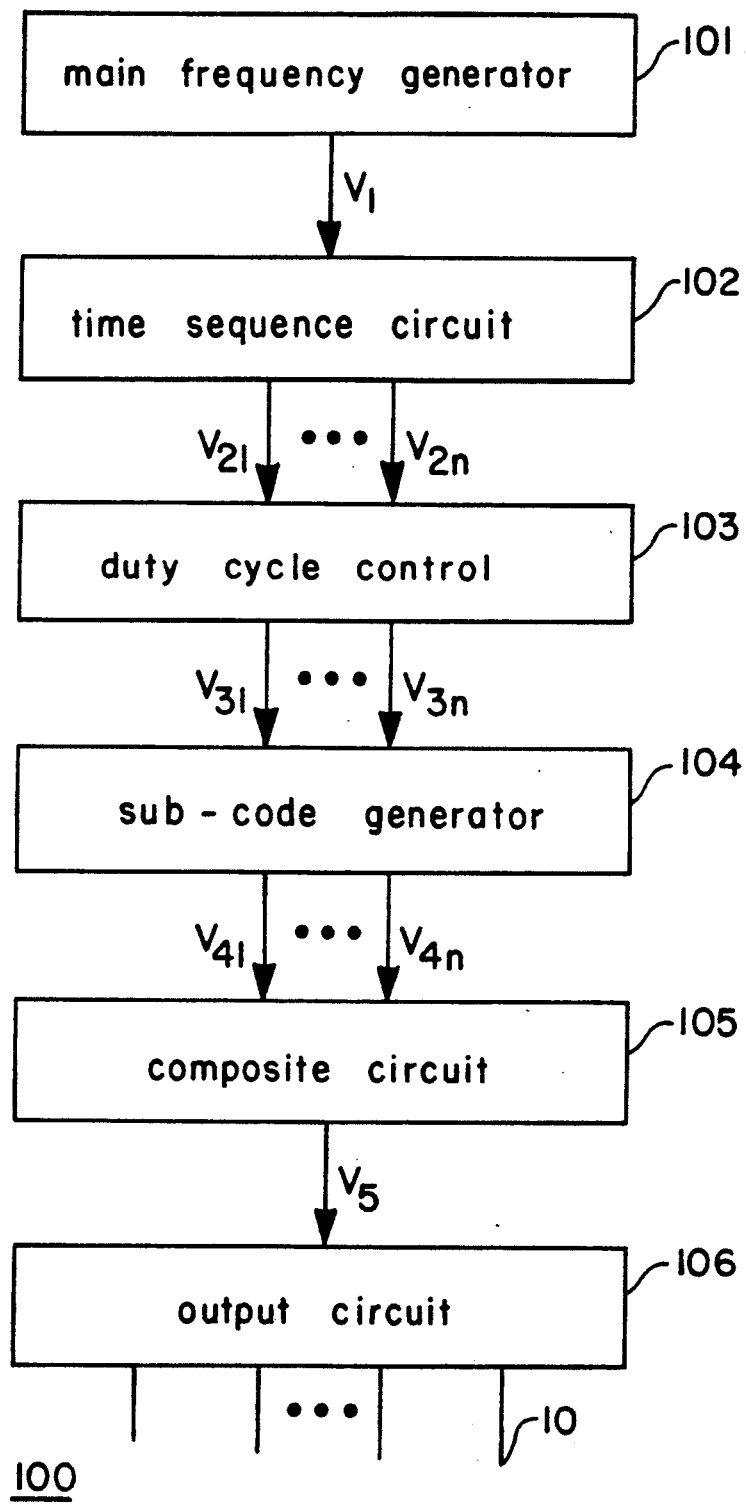
FIG. 2 is a block diagram showing the first embodiment of the apparatus according to the present invention.

Referring to FIG. 2, it shows a block diagram of the first embodiment of the apparatus according to the present invention. The reference numeral 100 indicates the apparatus as a whole; 101 indicates a main frequency generator which can be any conventional clock circuit with the frequency F of its output signal $V_1$ being a constant value in the range of 230-280 KHz; 102 indicates a time sequence circuit which generates n parallel time sequence signals $V_{21}$-$V_{2n}$ according to the time sequence number n of the desired vital information signals; 103 indicates a duty cycle control circuit which controls the duty cycle of the signals $V_{21}$-$V_{2n}$ generated by the time sequence circuit 102 to keep its outputs $V_{31}$-$V_{3n}$ within the required pulse width. A main code generating circuit is made up of the above-mentioned main frequency generator 101, time sequence circuit 102 and duty cycle control circuit 103. 104 indicates a group of sub-code generators which generate n parallel controlled sub-code signals $V_{41}$-$V_{4n}$ according to the signals $V_{31}$-$V_{3n}$ from the control circuit 103, wherein the pulse numbers of the sub-code signals are preset as $N_1$, $N_2$, ... $N_n$, respectively, and the duty cycle of the sub-code signals is preset as d. 105 indicates a composite circuit which combines the n parallel signals $V_{41}$-$V_{4n}$ from the sub-code generator 104 into a highly sequenced serial signal $V_5$ with the desired waveform. The waveform of signals $V_1$-$V_5$ is shown in FIG. 4, in which, as an example, $n=3$, $D=1.5$, $N_1=3$, $N_2=6$, $N_3=9$, $d=1.0$. 106 indicates an output circuit which divides, shapes and attenuates signal $V_5$ then sends it out through the electrodes 10.

Figure 3A:
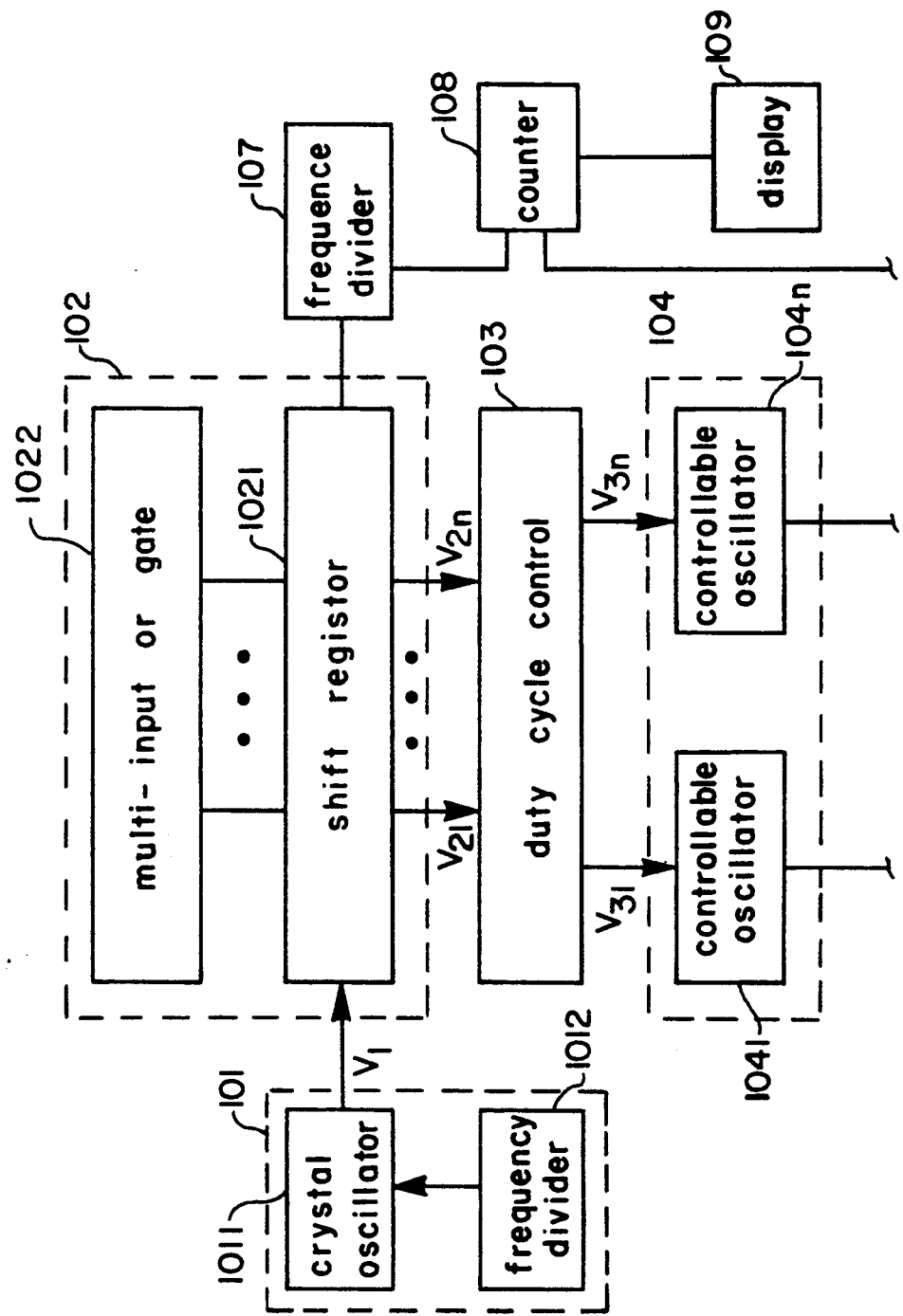
FIG. 3A-3B is a diagram showing a detailed circuit structure of the embodiment shown in FIG. 2.
Figure 3B:
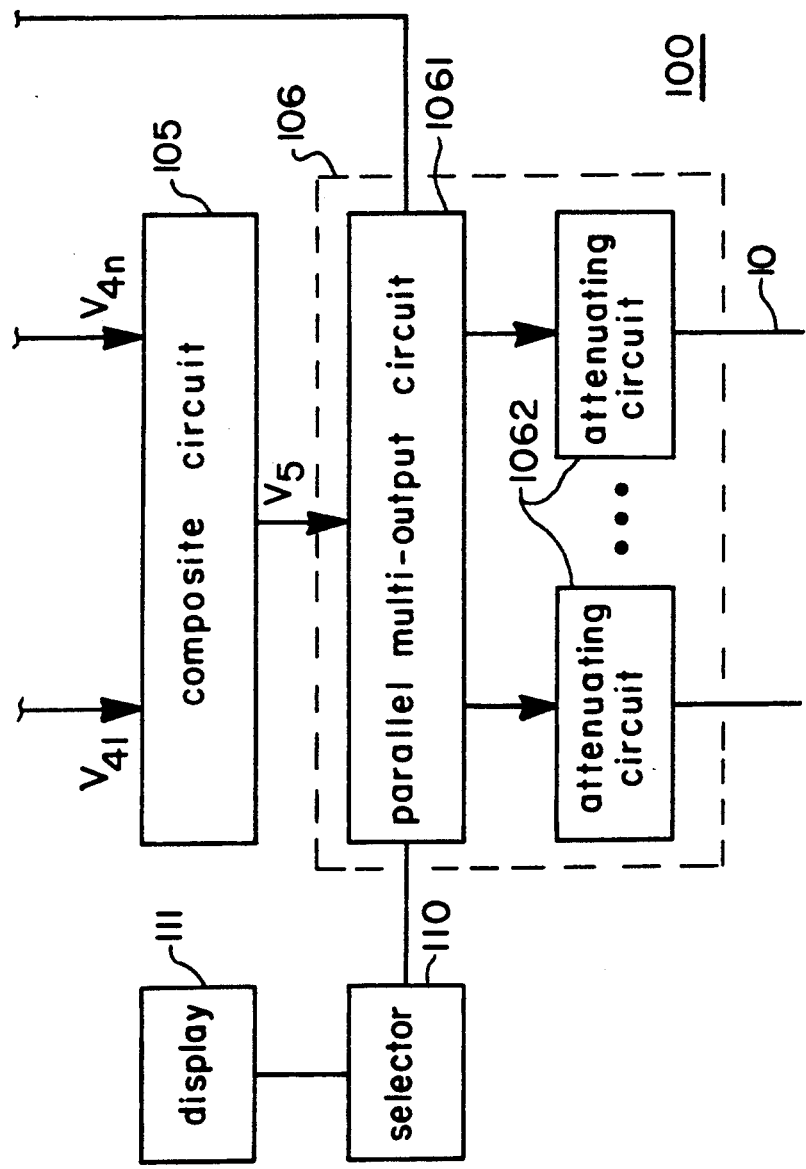

FIG. 3 is a diagram showing an example of the circuit of the embodiment shown in FIG. 2. In FIG. 3, the main frequency generator 101 comprises a crystal oscillator 1011 and a frequency divider 1012. The high frequency signal generated by the crystal oscillator 1011 is divided by frequency divider 1012 into a clock signal $V_1$, as shown in FIG. 4. The time sequence circuit 102 comprises a shift register 1021 and a multi-input OR gate 1022. When the sequence number n of the vital information signal is 2, the time sequence circuit 102 can also be formed by a dual "D" Flip Flop. The shift register 1021, actuated by the input signal $V_1$, sends out n parallel signals $V_{21}$-$V_{2n}$ according to the desired value of n; the waveform of the signals is shown in FIG. 4. The time sequence circuit 102 can also be made of a ring counter or a counter/decoder. The duty cycle control circuit 103 is made of monostable circuit which adjusts the width of the signals $V_{21}$-$V_{2n}$ to form signals $V_{31}$-$V_{3n}$ according to the desired D. The sub-code generator 104 comprises n parallel controllable oscillators 1041-104n, the frequency of each of the controllable oscillators 1041-104n being preset so that $N_1$-$N_n$ pulses can be sent out respectively within the pulse width of signals $V_{31}$-$V_{3n}$, as the signals $V_{41}$-$V_{4n}$ shown in FIG. 4. In FIG. 4, $N_1=3$, $N_2=6$ $N_3=9$. The parallel output of the sub-code generator 104 shown in FIG. 3 is composited into a serial signal $V_5$ through the composite circuit 105 made of a multi-input OR gate. The output 106 comprises a parallel multi-output circuit 1061 and a plurality of shaping and attenuating circuits 1062 which will be further explained hereinafter. In FIG. 3, there are also a frequency divider 107, a counter 108 and a display 109, which can count the number of the sub-code pulses in the vital information signals sent out by the apparatus during a fixed period. Thus errors in the signals can be shown on display 109, if any. An alarming device can also be added to prevent the errors in the signals. A selecting circuit 110 can be made of a selecting switch to select respectively corresponding signals sent out in a parallel manner from circuit 1061 and to display the signal level on the display 111. In the circuit shown in FIG. 3, each waveform parameter of the output signal $V_5$, such as F, D, $N_1$-$N_n$, and d, can be determined by presetting the frequency F of the main frequency generator 101, the pulse width P of the duty cycle control circuit 103, the frequencies $f_1$-$f_n$ and the duty cycle d of the controllable oscillators and the duty cycle d of the controllable oscillators 1041-104n, so as to guarantee the correct code structure of the waveform.

FIG. 5A-5C are block diagrams of the second embodiment of the apparatus according to the present invention. In FIG. 5A, the reference numeral 200 indicates the apparatus as a whole; the main frequency generator 101, the time sequence circuit 102, the output circuit 106 and electrodes 10 are the same with those shown in FIGS. 2 and 3. 201 indicates a coded pulse generating circuit and 202 indicates a code-controlling circuit. The coded pulse generating circuit 201 can be made of the practical circuits shown in FIG. 5B or 5C, which generates a burst with a predetermined frequency according to the input clock signal and control signals, while the code-controlling circuit 202 counts the pulse train sent out by the circuit 201. When the counting reaches a predetermined value, the code-controlling circuit 202 sends out a reset pulse which resets the coded pulse generating circuit 201 and the next burst with another specific frequency will be sent out after a predetermined time period. In this way, the coded pulse generating circuit 201, under the control of the circuit 202, generates a train of bursts, in which the frequency and the pulse number of each burst meet the predetermined coding requirements, as shown by Vc in FIG. 6. The code-controlling circuit 202 can be made of, for example, a presettable counter, a programmable counter, a counter/pulse-distributor, or a counter/divider; etc.

FIG. 5B shows a circuit structure of the coded pulse generating circuit 201 which comprises a charging current switch 2011, a discharging current switch 2012, a capacitor 2013, a pulse generator 2014 and n parallel constant current sources 2015. The pulse generator 2014 can be made of a time base circuit, a phase locked loop frequency divider or a programmable frequency divider, etc. Under the control of the code-controlling circuit 202, the constant current sources 2015 charge the capacitor 2013 through the charging current switch 2011. When the potential of the capacitor 2013 reaches a predetermined value, the charging current switch 2011 is opened while the discharging current switch 2012 is closed so as to discharge the capacitor 2013. In this way, a sawtooth wave is generated, as shown in FIG. 6. The slope of the sawtooth wave can be changed by adjusting the current intensity of the constant current sources 2015, thus the width of the sawtooth wave is changed; therefore, the times of charging-discharging of the current within a determined period can be changed. The signal $V_b$ is inputted into the pulse generator 2014 to generate signal $V_c$ which is counted by the code-controlling circuit 202, and the pulse generator 2014 is reset according to the counted value so as to guarantee the desired interval between the bursts.

The code pulse generating circuit shown in FIG. 5B can be replaced by a programmable frequency divider, as shown in FIG. 5C. The programmable frequency divider divides properly a high frequency clock signal according to a routine to generate pulses with a desired frequency. Under the control of the programmable component, different signal parameters can be set to generate the vital information signals which meet different coding requirements.

It can be seen by comparing FIG. 6 with FIGS. 1A-1E and FIG. 4 that signal Vd has the same structure as that of the main code shown in FIG. 1A. Its frequency F is determined by the main frequency generator 101 while its duty cycle D is determined by the coded pulse generating circuit 201 as well as the coding control circuit 202. Vc has the same structure as that of the pulse train of the vital information signals shown in FIG. 1C and $V_5$ of FIG. 4, wherein the number of the sub-code pulses enclosed within the envelope of the main code pulses is counted by the code-controlling circuit 202 and the counted result is controlled according to preset values or a program.

Figure 7:
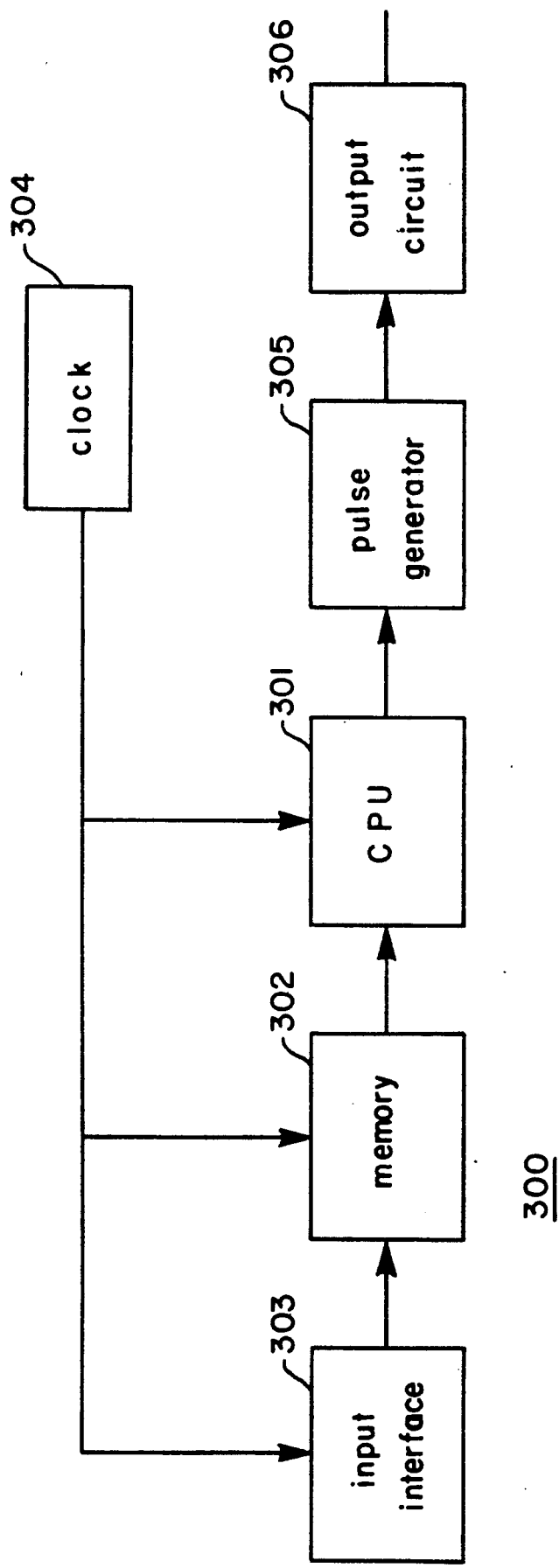
FIG. 7 is a block diagram showing the third embodiment of the apparatus according to the present invention.

The third embodiment of the apparatus according to the present invention is shown in FIG. 7 wherein the reference numeral 300 indicates the apparatus as a whole; 301 indicates a central processing unit CPU, 302 indicates a memory; 303 indicates an external input interface; 304 indicates a clock circuit which provides a timing signals for the system and works at a frequency of at least 30 MHz; 305 indicates a pulse generator, which generates under the real time control of the CPU 301 pulse signals that are sent out by the output circuit 106 after being shaped and attenuated.

Figure 8:
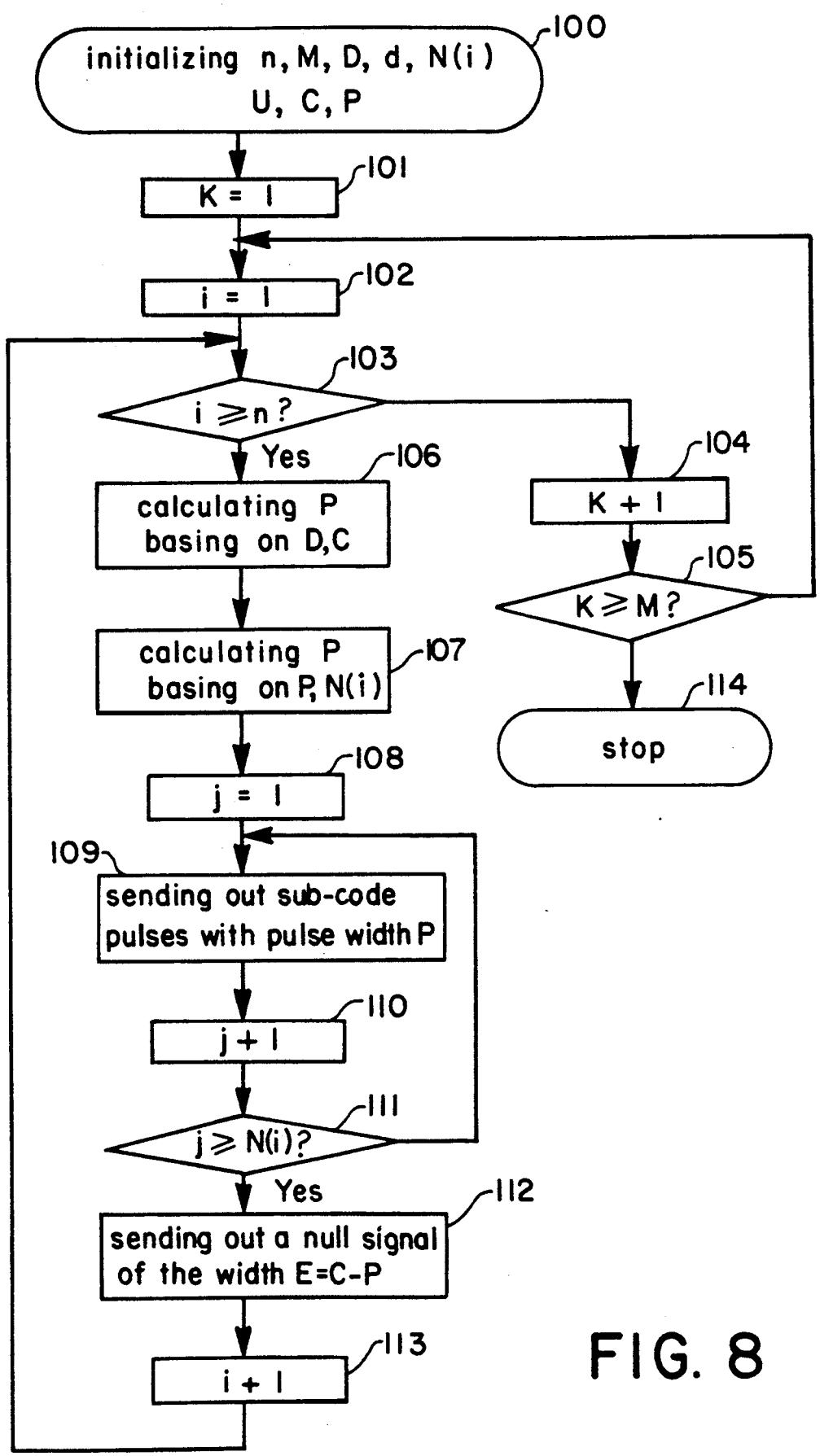
FIG. 8 is a flow chart of the apparatus shown in FIG. 7.

FIG. 8 shows a flow chart of the routine used in the apparatus 300. In this routine, step 100 inputs initial values into CPU 301, including the time sequence number n, number of cycles of the signal M, the duty cycle of the main code D, the duty cycle of the sub-code d, the number of sub-code pulses N(i), the signal's output level U, the main code time period C, the main code pulse width P ($C=P+E$, $D=P/E$). The meaning of each parameter is the same as that shown in FIGS. 1A-1E. Steps 101 and 102 are conventional setting steps. After discriminating at step 103 when 1<N, the routine comes to calculating steps. In step 106, $P=DC/(1+D)$ is calculated and in step 107 the subcode pulse width p is calculated by the equation $p = dP[N(i)(d+1)-1]$. In step 109, a control signal is sent out according to the sub-code pulse width P calculated, which signal makes the pulse generating circuit 305 generate a sub-code pulse with a pulse width p. Steps 109–111 repeat several times. When $j \geq N(i)$, the pulse generating circuit 305 generates the correct number of sub-code pulses, and then the routine comes to step 112. Step 112 controls the pulse generating circuit 305, which sends out a null signal during the period E ($E = C - P$). After step 113, the routine returns to step 103 and starts calculating and sending out sub-code pulses of the next main code pulse. When i=n, a complete vital information signal has been sent out and the routine, controlled by step 105, repeats the output of the vital information signal according to a predetermined number M.

Figure 9A:
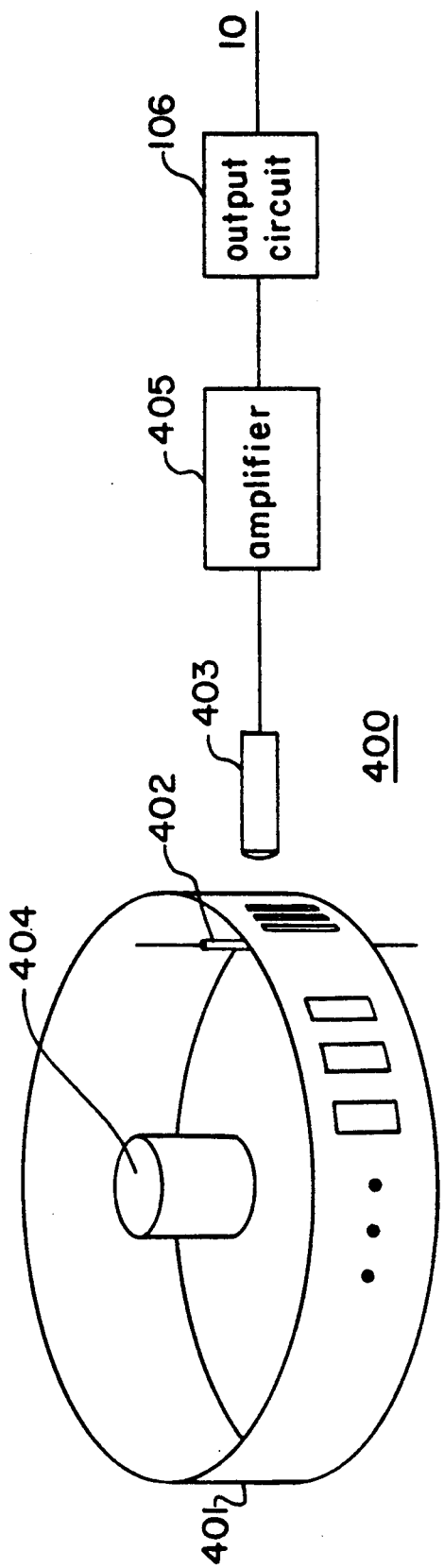
FIG. 9A and 9B are illustrative diagrams showing the fourth embodiment of the apparatus according to the present invention.
Figure 9B:
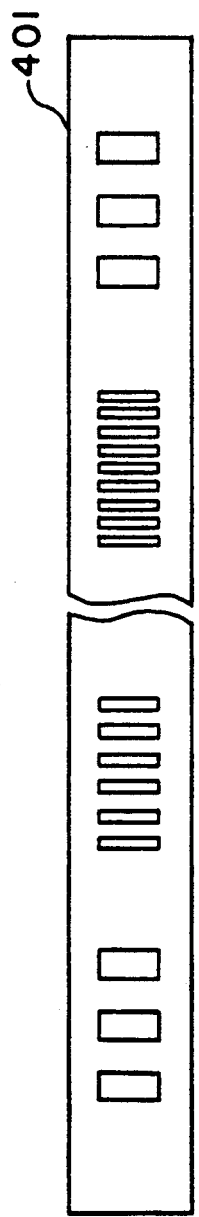

FIGS. 9A and 9B show the fourth embodiment of the apparatus according to the present invention, in which the reference numeral 400 indicates the apparatus as a whole; 401 indicates a light modulating device; 402 indicates a light source which can be any conventional or laser light source; 403 indicates a photosensitive device such as a photosensitive diode or a photosensitive FET, etc, with its photoelectric response time being $T < 10^{-8}S$, dark current $I < 10^{-8}A$, and photoelectric sensitivity $S > 100$ microampere/LX; 404 indicates a driving device, such as a high speed motor, which drives the light modulating device 401 to move relatively to the light source 402 and the photosensitive device 403; 405 indicates an amplifier circuit which amplifies the signal generated by the photosensitive device 403 and feeds it to the output circuit 106. A light grid formed on the light modulating device 401 has its width corresponding to the pulse waveform of the desired signal. As shown in FIG. 9B, when the light modulating device 401 driven by the driving device 404 moves relatively to the light source 402 and the photosensitive device 403, the light emitted from the light source 402 is modulated into a light pulse train similar to the desired pulse train. The photosensitive device 403 generates, corresponding to this light pulse train, a electric pulse train which can be sent out through the electrodes for medical and health care uses or through the amplifer 405 and the output circuit 106 to give it a proper level and then send it out multiply. Obviously, the light modulating device 402 can be changed from transmissive type shown in FIG. 9A into the reflective type and with corresponding rearrangement of the light source 401 and the photosensitive device 403. A simlar result can thus be achieved. In this embodiment, the main code frequency, duty cycle and the sub-code frequencies can be adjusted by changing the rotary speed of the driving device 404, the radius of the light modulating device 401 and the distance between the slots thereon.

Referring to FIG. 10, an illustrative diagram of the first embodiment of the method according to the present invention is shown, in which 501 indicates a signal output interface; 502 indicates a video signal reproducing apparatus, such as a video tape recorder, a laser disc player, etc; 503 indicates a video signal recording medium such as video tapes, laser discs, etc. the method includes the following steps:

1. recording the pulse train signals generated by any one of the embodiments of the apparatus according to the present invention on a video signal recording medium, such as a video tape or a laser disc, after proper adjusting of the level;
2. generating coded pulse train of the present invention by using the above-mentioned recording medium and a signal reproduction apparatus as the signal source;
3. feeding the generated pulse train through the signal output interface 501 to the output circuit 106; and
4. sending out the signals shaped and attenuated by the output circuit 106 through electrodes 10 for medical or health care uses.

Referring to FIG. 11, there is shown an illustrative diagram of the second embodiment of the method according to the present invention, in which 601 indicates an output interface; 602 indicates a computer which has a clock frequency of over 30 MHz; 603 indicates a memory medium for the program, such as a tape, a hard disc, a soft disc or the internal memory within the computer. The method includes the following steps:

1. programming the vital information signal according to the present invention by steps shown in the flow chart of FIG. 8;
2. generating the real time control signals by using computer 602 according to the waveform parameters inputted in the routine;
3. feeding the control signals through the interface 601 to the pulse generator 305 for generating desired coded pulse train signals;
4. shaping and attenuating the coded pulse train signals through the output circuit 106 and then sending out the signals for medical and health care uses.

Figure 12:
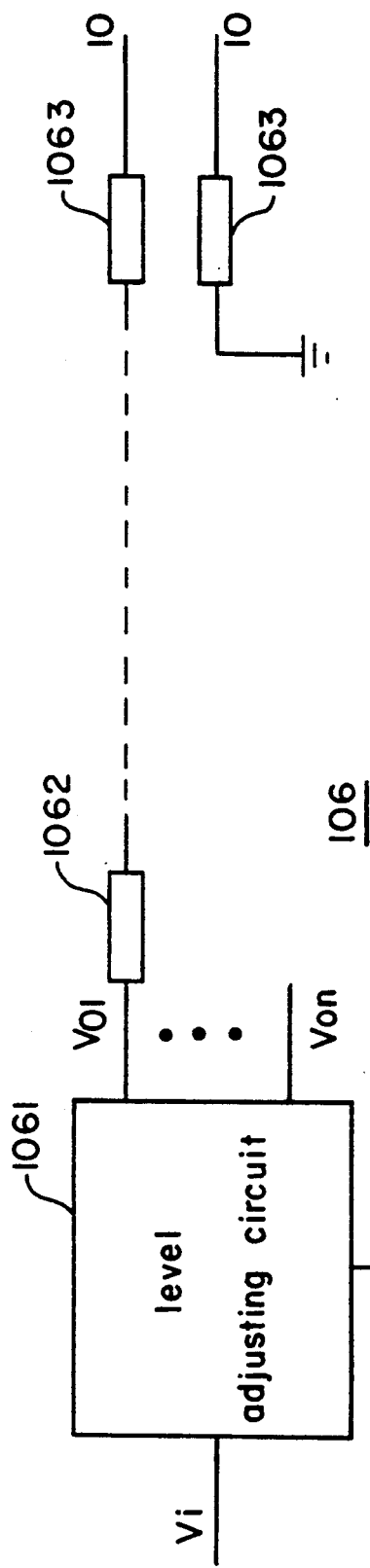
FIG. 12 is an illustrative diagram showing the output circuit according to the present invention.

Referring to FIG. 12, there is shown an illustrative diagram of the output circuit 106 of the present invention, in which 1061 indicates a level adjusting circuit, 1062 and 1063 are the signal attenuating device of the present invention, Vi is the input of the circuit, $V_{01}$-$V_{0n}$ are the n parallel outputs. The level adjusting circuit 1061 can adjust the level of the input signal $V_i$ in a relatively wide range (0–10 MHz) and shape its waveform then send it out through multiple outputs for the use of more than on patient. The signal attenuating devices 1062 and 1063 are resistive attenuating elements with their resistance being larger than $10^7$ ohm and their frequency response range being between 0 to 10 MHz. The signal attenuating device can be made of biological materials, such as a piece of dried blood vessel or peritonaeum after preservative treatment, so as to get the preferred output waveform. The biological materials can be obtained from animals such as rat, rabbit, or chicken. A piece of the material should be treated by any conventional antiseptic agent under sterilized conditions then sealed by any conventional sealing agent in a sealing member such as a glass or plastic tube with two ends of the piece being kept in direct contact with two electrodes which are led out of the sealing member. The piece of the biological material should be dried to keep the water contained therein less than 8 percent, preferably 4 percent. The length of the piece can be adjusted to obtain the desired resistance value. The made-ready attenuating device should be the inserting-type and should not be soldered under high temperature.

The output electrodes of the present invention include a positive one and a negative one which can be made of any conductive material, but preferably a acupuncture needle or a thin copper sheet, the latter can be used as a non-invasive electrode to avoid pain caused by the needle. When the vital information signals of the present invention are used for medical or health care purposes, the proper acupoints should be chosen as the address windows for information exchange according to patients' conditions. The blood vessel invasion of the needles can also be used, such as invading the positive electrode into an artery of one arm and the negative electrode into a vein of the opposite leg, so as to achieve better effects of the information exchange; however, to prevent harmful effects, the invasive application of the electrodes should be avoided if the signals are not properly shaped and attenuated.

The apparatus and method for generating the vital information signals according to the present invention have been described hereinbefore, the above examples being used only for the convenience of explaining and understanding. For those skilled in the art, many changes and modifications can be made to the above examples without departing from the scope and spirit of the present invention. Therefore, the scope of the present invention will not be limited to the above examples and shall only be determined by the claims attached hereinafter.

What is claimed is:

1. An apparatus for generating vital information signals and applying them to the body of a patient, comprising:

means for generating an electrical signal comprising a pulse train consisting of a series of bursts of pulses, wherein the bursts are regularly spaced in time, and wherein each burst is made up of a plurality of pulses, the number of pulses in each burst varying from one burst to the next in a predetermined manner, and the frequency of the pulses in each burst varying from one burst to the next in a manner corresponding to the variation in the number of pulses in each burst such that all of the bursts are of equal time duration, the range of frequencies of the pulses in the bursts making up the pulse train being between about 230 and about 280 KHz, and the duty cycle of said bursts in said pulse train being in the range of 0.33–5.0; and at least one pair of electrodes connected to said means for generating an electrical signal for applying said pulse train to the body of the patient.

2. A method for generating vital information signals, comprising the steps of:

recording vital information signals on an information recording medium, said information signals comprising a series of bursts of pulses of electromagnetic energy wherein the range of frequencies of said pulses in said bursts is between 230–280 kHz frequency, said bursts having a duty cycle;

reproducing said signals recorded on said information recording medium by a signal reproducing apparatus;

feeding said reproduced signals to an output circuit through an interface circuit;

shaping and attenuating said signals by said output circuit; and providing said signals through a pair of electrodes for medical and health care uses.

* * * * *